United States Patent [19]

Nakanishi et al.

[11] 4,245,050

[45] Jan. 13, 1981

[54] PROCESS FOR THE PREPARATION OF CHOLINE OXIDASE BY FERMENTATION

[75] Inventors: Toru Nakanishi, Atsugi; Yozo Machida, Machida, both of Japan

[73] Assignee: Kyowa Hakko Kogyo Co., Ltd., Tokyo, Japan

[21] Appl. No.: 60,282

[22] Filed: Jul. 25, 1979

Related U.S. Application Data

[63] Continuation of Ser. No. 853,458, Nov. 21, 1977, abandoned.

[30] Foreign Application Priority Data

Nov. 19, 1976 [JP] Japan .................................. 51-139120
Dec. 25, 1976 [JP] Japan .................................. 51-155655

[51] Int. Cl.$^3$ .............................................. C12N 9/06
[52] U.S. Cl. ........................................ 435/191; 435/25; 435/840; 435/843
[58] Field of Search .................... 435/192, 191, 25, 28

[56] References Cited

U.S. PATENT DOCUMENTS

| 4,087,329 | 5/1978 | Terada et al. ......................... 435/227 |
| 4,093,517 | 6/1978 | Masurekar et al. ................... 435/190 |
| 4,135,980 | 1/1979 | Ikuta et al. ............................ 435/18 |

OTHER PUBLICATIONS

Ikuta et al., Journal of Biochemistry, (Tokyo), vol. 82, pp. 1741–1749, 157–163, (1977).
Takayama et al., Rinsho Byori, (Clinical Pathology, vol. 24, p. 461, (1976).

*Primary Examiner*—Lionel M. Shapiro
*Attorney, Agent, or Firm*—Fitzpatrick, Cella, Harper & Scinto

[57] ABSTRACT

Choline oxidase is produced by fermentation of a microorganism belonging to the genus Brevibacterium or Corynebacterium and which is capable of producing choline oxidase. Choline oxidase is useful for the determination of choline.

7 Claims, 6 Drawing Figures

PROCESS FOR THE PREPARATION OF CHOLINE OXIDASE BY FERMENTATION

This is a continuation, of application Ser. No. 853,458 filed Nov. 21, 1977, abandoned.

BACKGROUND OF THE INVENTION

The present invention relates to a process for the preparation of choline oxidase by fermentation.

Heretofore, it has been known that choline oxidase is produced by a microorganism belonging to the genus Arthrobacter. Choline oxidase derived from the microorganism catalyzes the conversion of choline chloride to betaine. By the conversion, hydrogen peroxide is also formed. A method for determination of choline by measuring the amount of hydrogen peroxide formed by the conversion has been proposed [Rinsho Byori (Clinical Pathology) 24, 461 (1976)].

It has now been found that a remarkable amount of choline oxidase is produced in the culture liquor and especially in the microbial cells, of a microorganism capable of producing choline oxidase and belonging to the genus Brevibacterium or Corynebacterium when cultured in a nutrient medium.

An investigation of the properties of the thus produced choline oxidase has led to the finding that betaine aldehyde is produced by oxidation of choline in the presence of choline oxidase and that betaine aldehyde is further converted to betaine by the action of the enzyme. Accordingly, choline oxidase obtained by the present process is useful for the quantitative determination of choline.

SUMMARY OF THE INVENTION

In accordance with the present invention, choline oxidase is produced by culturing a microorganism belonging to the genus Brevibacterium or Corynebacterium which is capable of producing choline oxidase in a nutrient medium, accumulating choline oxidase in the culture liquor, and recovering said choline oxidase therefrom.

DESCRIPTION OF THE INVENTION

Figure 1:
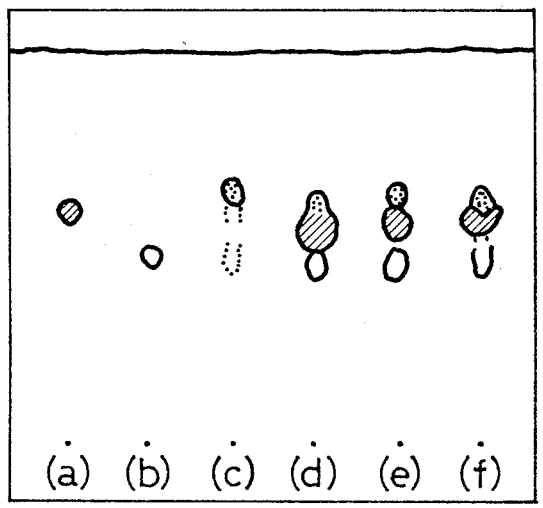
FIG. 1 illustrates the result of identification by thin layer chromatography of the reaction solution obtained by oxidation of choline in the presence of choline oxidase prepared by the process of the present invention.

In accordance with the present invention, any microorganism capable of producing choline oxidase and belonging to the genus Brevibacterium or Corynebacterium can be used. Particularly preferred microorganisms are found among those of the species *Brevibacterium album*, *Brevibacterium cerinum* and *Corynebacterium murisepticum*. Examples of favorable producers are *Brevibacterium album* KY 4319 (FERM-P No. 3777) (NRRL B-11,046) (ATCC 15,111), *Brevibacterium cerinum* KY 4320 (FERM-P No. 3778) (NRRL B-11,047) (ATCC 15,112) and *Corynebacterium murisepticum* KY 3505 (FERM-P No. 3779) (NRRL B-11,049) (ATCC 21,374). FERM-P indicates a deposit of a microorganism with the Fermentation Research Institute, Chiba-ken, Japan; NRRL indicates a deposit of a microorganism with the ARS Culture Collection Research Fermentation Laboratory, Peoria, Illinois, U.S.A. and ATCC is an abridgement of the American Type Culture Collection, Rockville, Maryland, U.S.A.

The bacteriological characteristics of *Brevibacterium album* KY 4319 and *Brevibacterium cerinum* KY 4320, and those of *Corynebacterium murisepticum* KY 3505 are described respectively in U.S. Pat. No. 3,222,258 and U.S. Pat. No. 3,630,842 which description is expressly incorporated herein.

In the present invention, either a synthetic medium or a natural medium may be used so long as it contains an assimilable carbon source, a nitrogen source, inorganic materials, and small amount of other nutrients which may be required by the specific strains used.

As the carbon source, choline or a salt thereof may be most preferably used. However, carbohydrate such as glucose, fructose, sucrose, molasses, etc., hydrocarbons such as n-paraffins, kerosene, etc., organic acids such as acetic acid, lactic acid, pyruvic acid, fumaric acid, etc., amino acids such as glutamic acid, aspartic acid, etc., may also be used.

As the nitrogen source, ammonia, inorganic and organic ammonium salts such as ammonium chloride, ammonium sulfate, ammonium phosphate, ammonium carbonate, ammonium acetate, etc., urea, monosodium glutamate, glycine, monosodium aspartate, choline, and other nitrogen-containing compounds, and peptone, meat extract, yeast extract, corn steep liquor, fish meal, soybean meal and other nitrogenous organic materials may be used depending upon the utilization by the microorganisms to be employed.

As the inorganic materials, potassium dihydrogen phosphate, dipotassium hydrogen phosphate, magnesium sulfate, sodium chloride, ferrous sulfate, manganese sulfate, potassium chloride, calcium carbonate, etc., are appropriate.

If a microorganism to be employed in the present invention requires specific nutrients for growth such as biotin, thiamine, etc., appropriate amounts of such nutrients must, of course, be supplemented to the medium. Sometimes, the nitrogenous organic materials to be employed as the nitrogen source may also serve as the source of the required nutrients. When such nitrogenous organic materials are employed, it is not necessary that the required nutrients be separately supplemented to the medium.

In the present invention, productivity of choline oxidase is increased by supplementing choline or a salt thereof to the medium as an inducer. Choline chloride, choline bromide, choline bicarbonate, choline citrate, choline ascorbate, and the like are appropriate salts. When choline or a salt thereof is used as an inducer, a preferred concentration in the medium is 7–800 mmol/L. In adding choline or a salt thereof as an inducer, it may be present in the initial medium or added during the course of culturing. When it is added during the course of culturing, it is preferable that the feeding be completed by the end of the logarithmic growth phase of the microorganism.

The following experimental example is illustrative of the determination of a preferred range of the amount of the inducer to be added to the medium.

The activity of choline oxidase in the experimental examples and the following examples is determined by oxidizing choline with choline oxidase to produce hydrogen peroxide, decomposing hydrogen peroxide with peroxidase in the presence of phenol and 4-aminoantipyrine to produce the pigment, and measuring the absorbancy of the pigment solution as described below.

A 0.05 mol/L Tris buffer solution (pH 8.0) containing 0.01 mol/L of 4-aminoantipyrine, 0.01 mol/L of phenol and 5000 U/L of peroxidase is prepared and used as color-forming liquid. To 3 ml of the color-forming liquid there is added 0.1 ml of enzyme solution to determine the activity and 0.1 ml of 1/30 mol/L choline chloride solution. Reaction is carried out at 37° C. for 20 minutes and then the absorbancy of the solution is measured at 500 nm. The amount of the reacted choline chloride is calculated based on the measured value. The enzyme activity is expressed by "U" which is defined as the amount of enzyme which will decompose 1 $\mu$mole of choline in 1 minute under the above-described conditions.

Experimental Example

In this experimental example, *Brevibacterium album* KY 4319 and *Corynebacterium murisepticum* KY 3505 are used. 10 ml portions of a nutrient medium having the following composition are poured into 70 ml-test tubes and sterilized at 120° C. for 15 minutes.

| choline chloride | various concentrations set forth in Table 1 |
|---|---|
| corn steep liquor | 0.5 g/dl |
| yeast extract | 0.5 g/dl |
| $K_2HPO_4$ | 0.1 g/dl |
| $MgSO_4 \cdot 7H_2O$ | 0.05 g/dl |
| monosodium glutamate | 0.5 g/dl |
| (pH 7.2) | |

One loopful of the above strains are separately inoculated into the medium in the test tubes, and culturing is carried out with shaking at 30° C. for 24 L hours.

After the completion of culturing, each of the culture liquors is subjected to centrifugation. The resultant microbial cells are suspended in 10 ml of 0.05 mol/L Tris buffer having a pH of 8.0 and disrupted by ultrasonic generator. The resultant mixture is subjected to centrifugation and choline oxidase activity of the supernatant is measured. The results are shown in Table 1.

TABLE 1

| Concentration of choline chloride (g/dl) | Strain | Activity of choline oxidase (U/dl) | |
|---|---|---|---|
| | | B. album KY 4319 | C. murisepticum KY 3505 |
| 0 | | 2.8 | 2.1 |
| 0.1(7.2 mmol/L) | | 13.0 | 6.4 |
| 0.5(36 mmol/L) | | 35.4 | 9.3 |
| 1.0(72 mmol/L) | | 32.7 | 17.1 |
| 2.0(144 mmol/L) | | — | 17.5 |
| 5.0(360 mmol/L) | | 23.4 | 12.8 |
| 10.0(720 mmol/L) | | 15.1 | 6.7 |

Culturing of the choline oxidase-producing microorganisms of the invention is carried out under aerobic conditions, for example, with shaking or with aeration and stirring. The suitable temperature range for culturing is 25°–35° C.; and the pH of the medium is preferably maintained in the range of 7.0–8.5. Usually, after 1–3 days of culturing, a considerable amount of choline oxidase is accumulated in the culture liquor, mainly in the microbial cells.

After the completion of culturing, the microbial cells are isolated from the culture liquor, for example, by centrifugation and disrupted by suitable means, for example, using an ultrasonic generator. The resultant mixture is subjected to centrifugation, etc. to obtain the supernatant. To recover choline oxidase from the supernatant, various methods usually used for the purification of enzymes such as salting out, precipitation by an organic solvent, dialysis, column chromatography using Sephadex (Sephadex is trademark for molecular sieve, derivatives of polysaccharide dextran, produced by Pharmacia Fine Chemicals Inc., U.S.A.), column chromatography using an ion exchange Sephadex (Sephadex having groups for ion exchange, produced by Pharmacia Fine Chemicals Inc., U.S.A.), column chromatography by ion exchange cellulose, etc. may be used.

The enzymatic properties of the choline oxidase derived from *Brevibacterium album* KY 4319 and *Corynebacterium murisepticum* KY 3505 are illustrated in the following Table 2.

TABLE 2

| Enzymatic properties | Choline oxidase* | Derived from B. album KY 4319 | Derived from C. murisepticum KY 3505 |
|---|---|---|---|
| Action | | Catalyzes oxidation of choline to betaine through betaine aldehyde. The reaction process is exhibited as follows. choline $\xrightarrow{O_2}$ betaine aldehyde $+H_2O_2$ betaine aldehyde $\xrightarrow[H_2O]{O_2}$ betaine $+H_2O_2$ | |
| Stable pH range (pH) | | 7.0–8.3 | around 8.0 |
| Optimum pH range for reaction (pH) | | 7.5–9.0 | 7.5–9.5 |
| Optimum temperature range for reaction (°C.) | | 20–35 | — |
| Substrate specificity (relative activity %) | choline chloride | 100 | 100 |
| | acetylcholine chloride | 0 | 0 |
| | sarcosine | 0 | 0 |
| | betaine | 0 | 0 |
| | glycine | 0 | 0 |
| | 2-dimethyl-aminoethanol | 7.3 | 8.5 |
| | 2-methyl-aminoethanol | 1.0 | 0 |
| | ethanolamine hydrochloride | 0 | 0 |
| Stable temperature range (°C.) | | 20–45 | — |
| Stabilizer | | EDTA | — |
| Inhibitor | | sodium azide | — |
| Molecular weight | | about 97,000 | — |
| Isoelectric point (pH) | | 4.05 | — |

*Derived from KY 4319 and KY 3505 by the methods of Examples 1 and 3 respectively.

The enzymatic properties in Table 2 are determined by the following methods.

(1) Action

In the following Experiment (1) and (2), choline oxidase, derived from *Brevibacterium album* KY 4319 is used.

Experiment (1)

Identification of the enzymatic reaction products by thin layer chromatography.

Choline oxidase is dissolved in 0.05 mol/L Tris buffer having a pH of 8.0 to make up a concentration of 17.0 U/ml. Then, 0.1 ml of the solution, 3.0 ml of 0.2 mol/L borate buffer having a pH of 9.0, 5 ml of 1 mol/L aqueous solution of choline chloride and 5 mg of peroxidase are mixed and allowed to react with shaking at 30° C. overnight.

The following sample solutions, including the above reaction solution, are each spotted in an amount of 5 μl on Avicel SF (trade mark for plate of cellulose thin layer chromatogram; produced by Funakoshi Yakuhin Co., Ltd., Japan) (20×20 cm). Sample solutions:

(a) 0.1 mol/L aqueous solution of choline chloride
(b) 0.1 mol/L aqueous solution of betaine
(c) 0.13 mol/L aqueous solution of betaine aldehyde
(d) the reaction solution
(e) mixture of the reaction solution and 0.1 mol/L aqueous solution of betaine (1:1 by volume)
(f) mixture of the reaction solution and 0.13 mol/L aqueous solution of betaine aldehyde (1:1 by volume)

Development is carried out using methanol, acetic acid and water (18:1:1 by volume). After development, the plate is air-dried and immersed once in Dragendorff's Reagent prepared according to the procedure described in Karel Macek, Pharmaceutical Applications of Thin-layer and Paper Chromatography published by Elsevier Publishing Co., Amsterdam-London-New York, p. 659 (1972). Then the plate is air-dried and diluted sulfuric acid is sprayed on the plate as a color reagent. The results are shown in FIG. 1, from which it is apparent that the products obtained by oxidation of choline using the enzyme are betaine aldehyde and betaine.

Experiment (2)

Oxygen uptake and hydrogen peroxide formation by the enzymatic reaction using choline chloride and betaine aldehyde:

Part 1—Oxygen uptake

In this experiment, 0.5 ml of aqueous solution of substrate (containing choline chloride or betaine aldehyde in an amount shown in Table 3) and 1.0 ml of 0.2 mol/L borate buffer (pH 8.0) containing 0.01 mol/L of 4-aminoantipyrine, 0.01 mol/L of phenol and 50 mg/L of peroxidase are put in the main compartment of a Warburg vessel (Mitamura Riken Co., Ltd., Japan). Then, 0.5 ml of 0.05 mol/L Tris buffer (pH 8.0) containing 1.5 U/ml of choline oxidase is put in the side arm, and reaction is carried out at 37° C. During the reaction, the amount of oxygen uptake (volume) is measured at regular intervals of time. The reaction is completed in 30–40 minutes. The ratio of the amount of oxygen uptake (μmol) to the amount of the charged substrate (μmol) is shown in Table 3.

TABLE 3

| Substrate | Amount of substrate [A] (μmol) | Amount of $O_2$ uptake [B] (μmol) | [B]/[A] |
|---|---|---|---|
| Choline chloride | 1.25 | 2.34 | 1.87 |
| | 2.50 | 4.72 | 1.89 |
| | 5.00 | 9.56 | 1.91 |
| Betaine aldehyde | 1.25 | 1.10 | 0.88 |
| | 2.50 | 2.31 | 0.92 |
| | 5.00 | 4.67 | 0.93 |

Part 2—Formation of hydrogen peroxide

In this experiment, 0.05 mol/L Tris buffer (pH 8.0) containing 0.001 mol/L of 4-aminoantipyrine, 0.001 mol/L of phenol and 50 mg/L of peroxidase is used as a color-forming liquid. To 1.9 ml of the color-forming liquid there is added 0.1 ml of an aqueous solution of substrate (containing choline chloride or betaine aldehyde in an amount shown in Table 4), 0.2 ml of 0.05 mol/L Tris buffer (pH 8.0) containing 3.5 U/ml of choline oxidase and 0.8 ml of water, and reaction is carried out at 37° C. for 20 minutes. The absorbancy of the reaction mixture is measured at 500 nm. The amount of hydrogen peroxide produced is calculated based on the measured value. The ratio of the amount of the hydrogen peroxide produced (μmol) to the amount of the charged substrate (μmol) is shown in Table 4.

TABLE 4

| Substrate | Amount of substrate [A'] (μmol) | Amount of hydrogen [B'] peroxide (μmol) | [B']/[A'] |
|---|---|---|---|
| Choline chloride | 0.045 | 0.081 | 1.80 |
| | 0.090 | 0.150 | 1.67 |
| | 0.180 | 0.310 | 1.72 |
| Betaine aldehyde | 0.045 | 0.035 | 0.78 |
| | 0.090 | 0.084 | 0.93 |
| | 0.180 | 0.168 | 0.93 |

From Table 3, it is found that the amount of oxygen consumed by 1 mol of choline chloride is 1.87–1.91 mol and from Table 4, it is found that the amount of hydrogen peroxide produced from 1 mol of choline chloride is 1.67–1.80 mol. Therefore, it is concluded that 2 mol of hydrogen peroxide is produced from 1 mol of choline chloride consuming 2 mol of oxygen. Similarly, it is concluded that 1 mol of hydrogen peroxide is produced from 1 mol of betaine aldehyde consuming 1 mol of oxygen.

From the results of Experiments (1) and (2), it is understood that the choline oxidase of the present invention has the action described in Table 2.

(2) Stable pH Range

Choline oxidase is dissolved in 0.05 mol/L Tris buffer having a pH of 8.0 to make a specific concentration (1.5 and 0.9 U/ml respectively in case of choline oxidase derived from KY 4319 and KY 3505 strains). Then, 0.5 ml portions of the solution are mixed with 1 ml portions of 0.05 mol/L Tris buffer having various pH values to make up solutions having different pH values between 5 and 10. The thus prepared solutions are kept at 45° C. for 30 minutes and then subjected to determination of choline oxidase. The relative enzymatic activities are calculated by defining the highest activity thus obtained as 100. The results are shown in FIG. 2.

Figure 2:
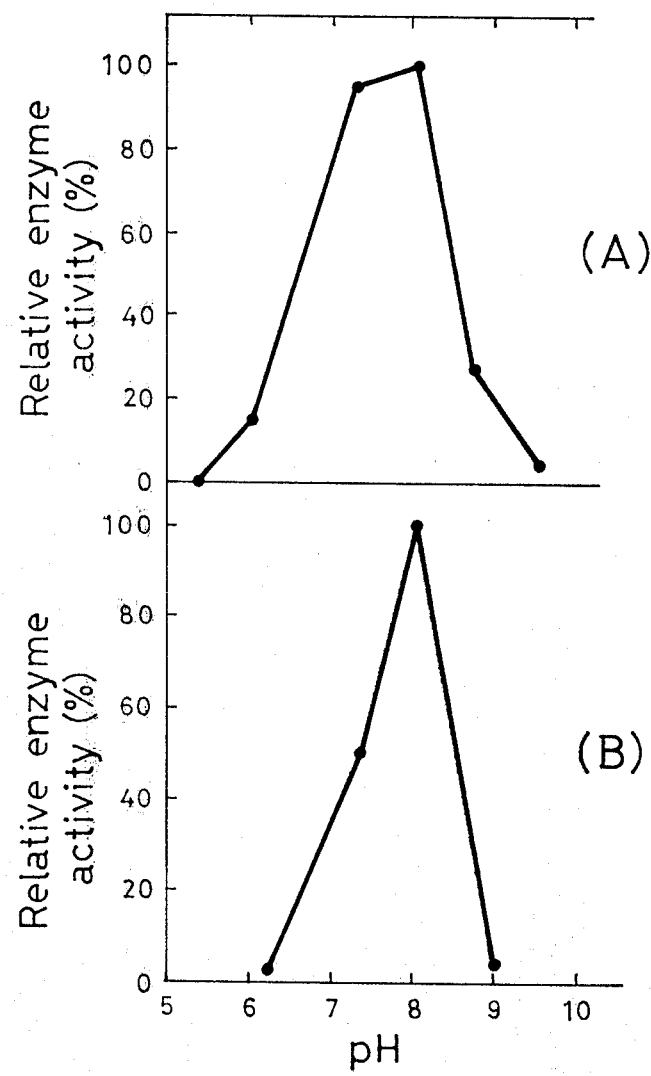
FIG. 2 illustrates the stable pH range of choline oxidase prepared by the process of the present invention.

In FIG. 2, (A) and (B) denote the test results of the enzymes obtained from cells of *Brevibacterium album*

KY 4319 and *Corynebacterium murisepticum* KY 3505 respectively.

(3) Optimum pH Range for Reaction

An approximately 4 ml-reactor for measurement of oxygen absorption (produced by Kyusui-Kagaku Kenkusho Co., Ltd., Japan) is kept at specific temperature (30° and 30° C. respectively in case of choline oxidase derived from KY 4319 and KY 3505 strains) and an oxygen electrode is inserted therein.

Figure 3:
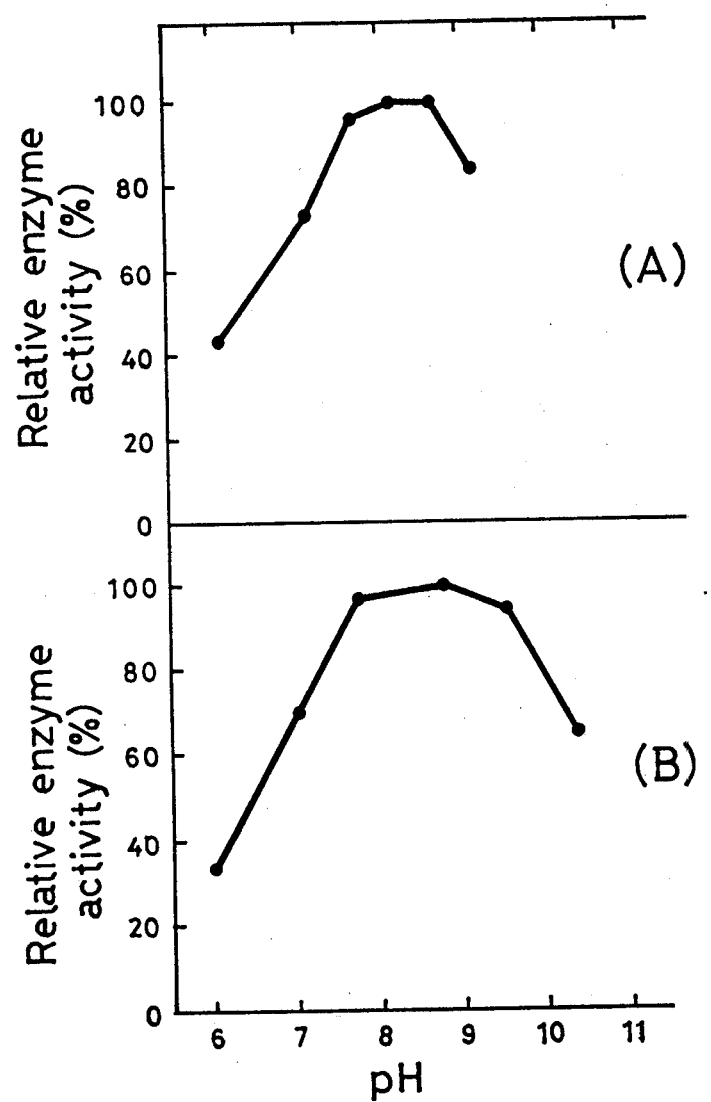
FIG. 3 illustrates the optimum pH range for reaction of choline oxidase prepared by the process of the present invention.

Choline oxidase is dissolved in 0.05 mol/L Tris buffer having a pH of 8.0 to make a specific concentration (2.3 and 1.2 U/ml respectively in case of choline oxidase derived from KY 4319 and KY 3505 strains). Then, portions comprising 0.1 ml of the resultant enzyme solution, 0.1 ml of 0.1 mol/L choline chloride aqueous solution and 3.6 ml of 0.05 mol/L Tris buffer having different pH values between 6 and 11 are poured into the reactor and stirred. The concentration of oxygen dissolved in the solution is recorded continuously by recorder (Desk Top Recorder, produced by Okura Denki Co., Ltd., Japan). Decrease in oxygen concentration between 30 seconds and 3 minutes after initiation of the reaction is calculated. Relative enzyme activities are calculated by defining the maximum decrease among the decreases obtained with the solutions having different pHs as an enzyme activity of 100. The results are shown in FIG. 3 wherein (A) and (B) have the same meaning as described in the above item (2).

(4) Optimum Temperature Range for Reaction

Figure 4:
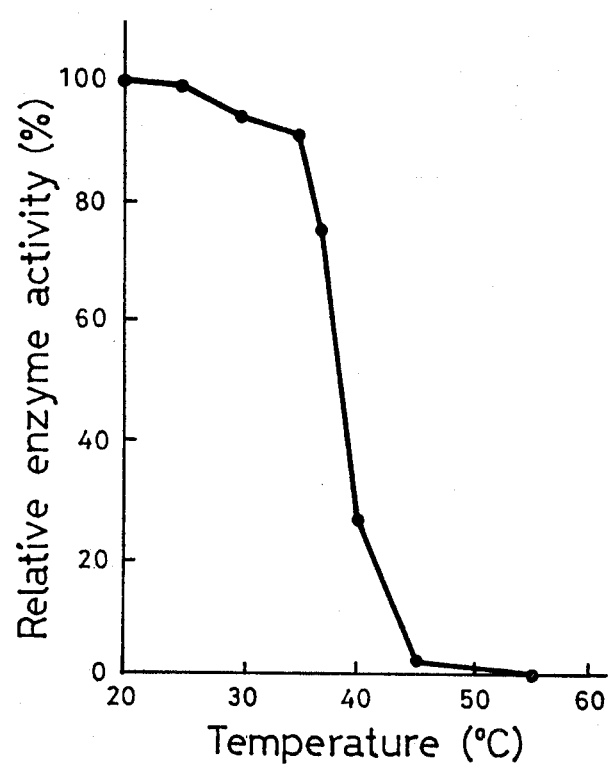
FIG. 4 illustrates the optimum temperature range for the reaction of choline oxidase prepared by the process of the present invention.

Choline oxidase is dissolved in 0.05 mol/L Tris buffer having a pH of 8.0 to make up a specific concentration of 1.2 U/ml. Portions of the solution are subjected to the same determination of choline oxidase as described above except that the reaction is carried out at different temperatures between 20° and 60° C. Relative enzyme activities are calculated by defining the highest enzyme activity among the activities obtained at the different temperatures as 100. The results are shown in FIG. 4.

(5) Substrate Specificity

Choline oxidase is dissolved in 0.05 mol/L Tris buffer having a pH of 8.0 to make up a specific concentration (1.5 and 0.4 U/ml respectively in case of choline oxidase derived from KY 4319 and KY 3505 strains). The solutions are then subjected to the same determination of choline oxidase as described above except that the various substances other than choline chloride shown in Table 3 are used as a substrate. The relative activities on the various substrates are calculated by defining the activity on choline chloride as 100.

(6) Stable Temperature Range

Figure 5:
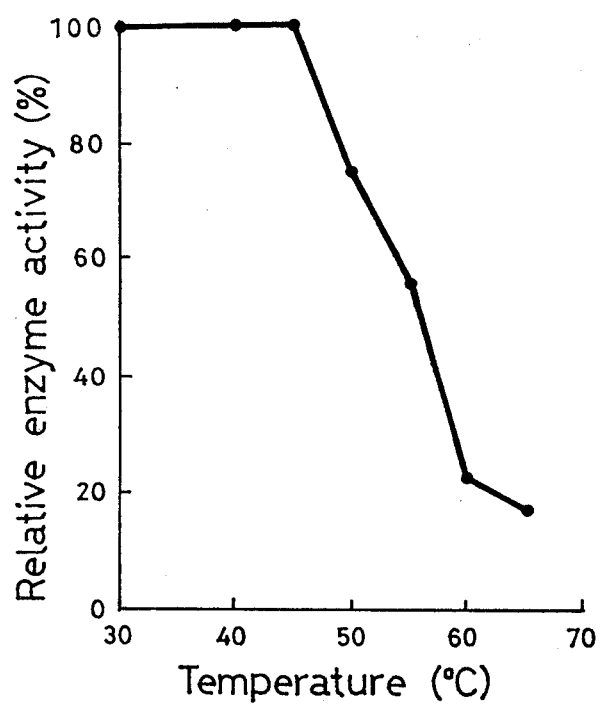
FIG. 5 illustrates the stable temperature range of choline oxidase prepared by the process of the present invention.

Choline oxidase is dissolved in 0.05 mol/L Tris buffer having a pH of 8.0 to make a concentration of 2.2 U/ml. Portions of the resultant solution are respectively kept at 30°, 40°, 45°, 50°, 55°, 60° and 65° C. for 30 minutes and then cooled. The cooled solutions are subjected to the determination of choline oxidase. The relative enzyme activities at the various temperatures are calculated by defining the enzyme activity at 30° C. as 100. The results are shown in FIG. 5, from which it is found that about 84% loss in activity is caused by treatment at 65° C. for 30 minutes.

(7) Stabilizers

Figure 6:
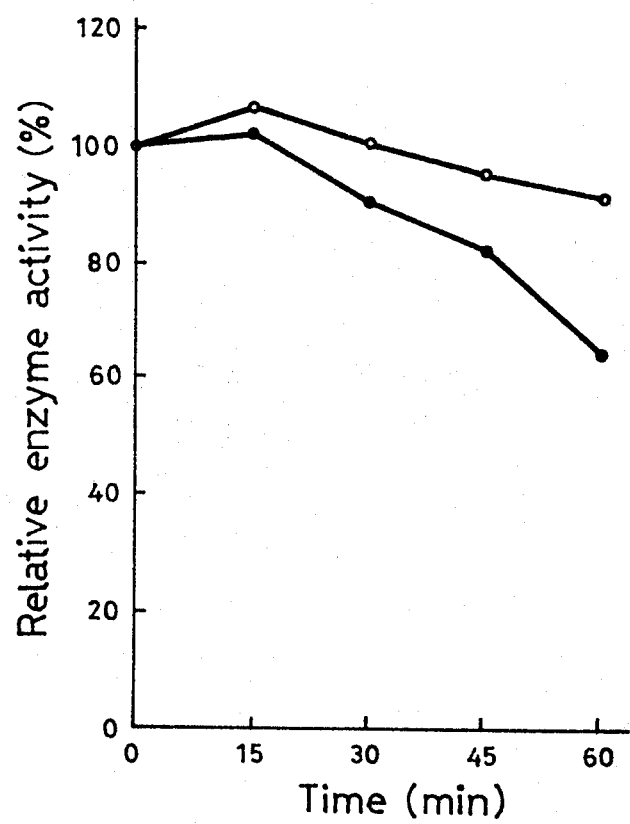
FIG. 6 illustrates the stabilizing activity of EDTA on choline oxidase prepared by the process of the present invention.

Choline oxidase and EDTA are dissolved in 0.05 mol/L Tris buffer having a pH of 8.0 to make up respective concentrations of 2.2 U/ml and $10^{-3}$ mol/L. Separately, choline oxidase is dissolved in 0.05 mol/L Tris buffer having a pH of 8.0 to make up a concentration of 2.2 U/ml (control). Portions of the resultant solution as it is, and portions of the solution obtained by maintaining it at 45° C. for 15, 30, 40 or 60 minutes and then cooling are subjected to determination of choline oxidase. The relative enzyme activities are calculated by defining the enzyme activity in case of no heat treatment as 100. The results are shown in FIG. 6 wherein o—o denotes EDTA addition and •—• denotes no EDTA addition. It is found from FIG. 6 that EDTA has a choline oxidase-stabilizing activity.

(8) Inhibitors

An approximately 4 ml-reactor for measurement of oxygen absorption is kept at 37° C. and an oxygen electrode is inserted therein. Choline oxidase is dissolved in 0.05 mol/L Tris buffer having a pH of 8.0 to make up a concentration of 0.8 U/ml. Then 0.1 ml of the resultant enzyme solution, 50 µl of 1 mol/L choline chloride aqueous solution, 0.1 ml of $1.7 \times 10^{-3}$ mol/L sodium azide aqueous solution and 3.5 ml of 0.05 mol/L Tris buffer having a pH of 8.0 are poured into the reactor. The concentration of oxygen dissolved in the solution is recorded continuously by recorder while stirring the solution. Decrease in oxygen concentration for 5 minutes after the start of the reaction is calculated.

The same procedure as above is repeated except that sodium azide is not added (control).

As the result, it is found that the enzyme activity is inhibited by 44.4% by $1.7 \times 10^{-3}$ mol/L sodium azide as compared with the control.

(9) Molecular Weight

The molecular weight of choline oxidase is determined according to the gel-filtration method [Biochemical Journal 96 595 (1965)] using sephadex G 200 (trade mark for molecular sieve, produced by Pharmacia Fine Chemicals Inc., U.S.A.). As the result, the enzyme of the invention is determined to have a molecular weight of about 97,000.

(10) Isoelectric Point

The isoelectric point of choline oxidase is determined according to the electrofocusing method under the following conditions.
Carrier ampholite: having pHs of 3.5–5.0
Column volume: 110 ml
Time charged with electricity: 24 hours
Fraction: 2 g As the result, the enzyme of the invention is determined to have an isoelectric point of pH 4.05.

Certain specific embodiments of the invention is further illustrated by the following representative examples.

EXAMPLE 1

In this example, *Brevibacterium album* KY 4319 (NRRL B-11,046) is used as a seed strain. Ten ml of a seed medium having the following composition is poured into a 70 ml-test tube and sterilized at 120° C. for 15 minutes:

Choline chloride 2 g/dl, corn steep liquor 0.5 g/dl, yeast extract 0.5 g/dl, monosodium glutamate 0.5 g/dl, $K_2HPO_4$ 0.1 g/dl, $MgSO_4.7H_2O$ 0.05 g/dl (pH 7.2)

One loopful of the strain is inoculated into the seed medium and cultured with shaking at 30° C. for 48 hours. The entire culture liquor is then transferred to 300 ml of the same seed medium as above in a 2 L-Erlenmeyer flask and cultured with shaking at 30° C. for 48 hours.

The entire culture liquor is again transferred to 3.0 L of a medium having the same composition as that of the seed medium in a 5-jar fermenter. Culturing is carried out at 30° C. for 24 hours with aeration of 1 L/L of medium/min and stirring at 500 r.p.m. After the completion of culturing, 0.62 U/ml of choline oxidase is accumulated in the culture liquor (calculated by the choline oxidase activity of the below described supernatant).

The culture liquor is subjected to centrifugation to separate out the micobial cells which are then suspended in 1 L of 0.05 mol/L Tris buffer having a pH of 8.0. The suspension is treated with Dyno Laboratory mill (KDL type) (produced by Willy A, Bachofen Inc., Switzerland) to obtain a mixture containing disrupted cells. Then, the mixture is subjected to centrifugation to obtain a supernatant to which is added ammonium sulfate to 30% saturation to form precipitates. The resultant mixture is subjected to centifugation, and ammonium sulfate is added to the supernatant to 60% saturation. The resultant precipitates are separated by centifugation and dissolved in 0.05 mol/L Tris buffer having a pH of 8.0. The solution is dialysed against the same Tris buffer as above at 5° C. overnight using a cellophane tube. After dialysis, the solution is charged onto a column of 1 L DEAE cellulose equilibrated with 0.05 mol/L Tris buffer (pH 8.0) containing 0.05 mol/L sodium chloride. After washing the resin with 1 L of 0.05 mol/L Tris buffer (pH 8.0) containing 0.05 mol/L sodium chloride, gradient elution is carried out with 0.05 mol/L Tris buffer containing sodium chloride while varying the concentration of sodium chloride from 0.05 to 0.45 mol/L.

The eluate is taken in fractions and the fractions containing choline oxidase are combined. To the combined solution ammonium sulfate is added to 60% saturation. The resultant precipitates are separated by centrifugation and dissolved in 0.05 mol/L Tris buffer having a pH of 8.0.

The thus obtained solution is charged onto a column of 500 ml of Sephadex G-150 (trade mark for molecular sieve; produced by Pharmacia Fine Chemicals Inc., U.S.A.) equilibrated with 0.05 mol/L Tris buffer (pH 8.0). Elution is carried out using the same buffer as above and the eluate is taken in fractions. The fractions containing choline oxidase are combined. To the combined solution ammonium sulfate is added to 60% saturation. The resultant precipitates are separated by centrifugation and dissolved in 0.05 mol/L Tris buffer having a pH of 8.0. The solution is dialyzed against the same buffer as above at 5° C. overnight using a cellophane tube. After dialysis, the solution is charged onto a column of 500 ml of DEAE Sephadex A-50 (trade mark for weakly basic anion exchange resin; produced by Pharmacia Fine Chemicals Inc., U.S.A.) equilibrated with 0.05 mol/L Tris buffer (pH 8.0) containing 0.1 mol/L sodium chloride. After washing the resin with 500 ml of 0.05 mol/L Tris buffer (pH 8.0) containing 1.0 mol/L sodium chloride, gradient elution is carried out with 0.05 mol/L Tris buffer containing sodium chloride while varying the concentration of sodium chloride from 0.1 to 0.5 mol/L.

The eluate is taken in fractions. The fractions containing choline oxidase are combined and dialyzed against 0.05 mol/L Tris buffer having a pH of 8.0 at 5° C. overnight using a cellophane tube. After dialysis, the solution is freeze-dried, whereby choline oxidase is obtained in about 10% activity yield. The product exhibits a specific activity of 2.2 U/mg of protein.

EXAMPLE 2

In this example, *Brevibacterium cerinum* KY 4320 (NRRL B-11,047) is used as a seed strain, and 300 ml of a medium having the following composition poured into a 2 L-Erlenmeyer flask and sterilized at 120° C. for 15 minutes is used:

Choline chloride 2 g/dl, corn steep liquor 1 g/dl, monosodium glutamate 0.2 g/dl, $K_2HPO_4$ 0.1 g/dl, $MgSO_4.7H_2O$ 0.05 g/dl (pH 7.2).

One loopful of the strain is inoculated in the medium and cultured with shaking at 30° C. for 48 hours. After the completion of culturing, 0.36 U/ml of choline oxidase is accumulated in the culture liquor.

EXAMPLE 3

In this example, the procedure described in Example 1 are repeated except that *Corynebacterium murisepticum* KY 3505 (NRRL B-11,049) is used.

After the completion of the main culturing step, 0.56 U/ml of choline oxidase is accumulated in the culture liquor. After purification, choline oxidase preparate is obtained in about 10% activity yield. The product exhibits a specific activity of 3.5 U/mg of protein.

EXAMPLE 4

In this example, *Brevibacterium album* KY 4319 is used as a seed strain. 10 ml of a medium having the following composition is poured into a 70 ml-test tube and sterilized at 120° C. for 15 minutes.

Composition of the Medium

Choline chloride 2 g/dl, glucose 0.5 g/dl, corn steep liquor 0.5 g/dl, yeast extract 0.5 g/dl, monosodium glutamate 0.5 g/dl, $K_2HPO_4$ 0.1 g/dl, $MgSO_4.7H_2O$ 0.05 g/dl (pH 7.2).

One loopful of the strain is inoculated into the medium and cultured with shaking at 30° C. for 48 hours. After the completion of culturing, 0.11 U/ml of choline oxidase is accumulated in the culture liquor.

Choline oxidase obtained by the process of the present invention is useful for the determination of choline in a sample. That is, choline may be determined by measuring amount of hydrogen peroxide formed by the oxidation of choline in the presence of choline oxidase.

What is claimed is:

1. A process for preparing choline oxidase which comprises culturing a microorganism belonging to the species *Brevibacterium album, Brevibacterium cerinum* or *Corynebacterium murisepticum* and being capable of producing choline oxidase when cultured in a nutrient medium, accumulating choline oxidase in the culture liquor, and recovering said choline oxidase.

2. A process according to claim 1 wherein said microorganism is selected from the group consisting of *Brevibacterium album* KY 4319 (FERM-P No. 3,777) (NRRL B-11,046) (ATCC 15,111), *Brevibacterium cerinum* KY 4320 (FERM-P No. 3,778) (NRRL B-11,047)

(ATCC 15,112) and *Corynebacterium murisepticum* KY 3505 (FERM-P No. 3,779) (NRRL B-11,049) (ATCC 21,374).

3. A process according to claim 1 wherein said nutrient medium contains choline or a salt thereof.

4. A process according to claim 3 wherein said nutrient medium contains from 7 to 800 mmol/L of choline or a salt thereof.

5. A process according to claim 1 wherein said culturing step is carried out at a temperature of from 25° C. to 35° C. and at a pH of from 7.0 to 8.5.

6. A process according to claim 1 wherein said recovery step includes separation and disruption of the microbial cells.

7. Choline oxidase produced by a microorganism belonging to the species *Brevibacterium album*, *Brevibacterium cerinum* or *Corynebacterium murisepticum* characterized by (a) catalyzing oxidation of choline to betaine aldehyde and that of betaine aldehyde to betaine; (b) a stable pH range of 7.0 to 8.3; (c) an optimum pH range for reaction of 7.5 to 9.0; (d) an optimum temperature range for reaction of 20° to 35° C.; (e) a stable temperature range of 20° to 45° C.; (f) a substrate specificity to choline or a salt thereof, a slight specificity to 2-dimethylaminoethanol, and no specificity to acetylcholine chloride, sarcosine, betaine, glycine, 2-methylaminoethanol and ethanolamine hydrochloride; (g) being stabilized by EDTA; (h) being inhibited by sodium azide; (i) a molecular weight of about 97,000; and (j) an isoelectric point of pH 4.05.

* * * * *